United States Patent [19]

Pritchett et al.

[11] Patent Number: 5,714,666
[45] Date of Patent: Feb. 3, 1998

[54] MEASUREMENT OF INTRACELLULAR CALCIUM USING BIOLUMINESCENT APOAEQUORIN EXPRESSED IN MAMMALIAN CELLS

[75] Inventors: Dolan B. Pritchett, deceased, late of Gibbsboro, N.J., by Sharon Barbara Newton Pritchett, executrix; Yeong-An Sheu, Cliffside Park, N.J.

[73] Assignees: Children's Hospital of Philadelphia; The Trustees of the University of Pennsylvania, both of Philadelphia, Pa.

[21] Appl. No.: 396,200

[22] Filed: Feb. 28, 1995

Related U.S. Application Data

[63] Continuation-in-part of Ser. No. 34,015, Mar. 22, 1993, abandoned, which is a continuation of Ser. No. 15,653, Feb. 9, 1993, abandoned.

[51] Int. Cl.$^6$ .............................. A01K 67/00; C12N 15/00
[52] U.S. Cl. .................. 800/2; 800/DIG. 1; 800/DIG. 2; 800/DIG. 3; 800/DIG. 4; 435/172.3
[58] Field of Search .............................. 435/240.2, 7.7, 435/325; 800/2, DIG. 1–4; 514/44; 424/93.1, 93.21

[56] References Cited

U.S. PATENT DOCUMENTS

| | | | |
|---|---|---|---|
| 4,873,191 | 10/1989 | Wagner et al. | 435/172.3 |
| 4,985,352 | 1/1991 | Julius et al. | 435/6 |
| 5,071,773 | 12/1991 | Evans et al. | 436/501 |

FOREIGN PATENT DOCUMENTS 0 341 477 A1  11/1989  European Pat. Off.

OTHER PUBLICATIONS

Bonner, "The Molecular Basis of Muscarinic Receptor Diversity", TINS 12, 148–151 (1989).
Campbell et al., "Formation of the $Ca^{2+}$–activated Photoprotein Obelin From Apo–obelin and mRNA Inside Human Neutrophils", Biochem. J. 252, 143–149 (1988).
Chen and Okayama, "High–Efficiency Transformation of Mammalian Cells by Plasmid DNA", Mol. Cell Biol. 7, 2745–2752 (1987).
Chomczynski and Sacchi, "Single–Step Method of RNA Isolation by Acid Guanidinium Thiocyanate–Phenol–Chloroform Extraction", Analytical Biochemistry 162, 156–159 (1987).
Cobbold and Rink, "Fluorescence and Bioluminescence Measurement of Cytoplasmic Free Calcium", Biochem. J. 248, 313–328 (1987).
Cotecchia et al., "Molecular Cloning and Expression of the cDNA for the Hamster $\alpha_1$–adrenergic Receptor", Proc. Natl. Acad. Sci. U.S.A. 85, 7159–7163 (1988).
Grynkiewicz et al., "A New Generation of $Ca^{2+}$ Indicators with Greatly Improved Fluorescence Properties", J. Biol. Chem. 260 3440–3450 (1985).

Gudermann et al., "Evidence for Dual Coupling of the Murine Luteinizing Hormone Receptor to Adenylyl Cyclase and Phosphoinositide Breakdown and $Ca^{2+}$ Mobilization", J. Biol. Chem. 267, 4479–4488 (1992).
Hori et al., "Structure of Native *Renilla Reniformis* Luciferin", Proc. Natl. Acad. Sci. U.S.A. 74, 4285–4287 (1977).
Inouye et al., "Expression of Apoaequorin Complementary DNA in *Escherichia coli*", Biochemistry 25, 8425–8429 (1986).
Inouye et al., "Cloning and Sequence Analysis of cDNA for the Luminescent Protein Aequorin" Proc. Natl. Acad. Sci. U.S.A. 82, 3154–3158 (1985).
Julius et al., "Molecular Characterization of a Functional cDNA Encoding the Serotonin 1c Receptor", Science 241, 558–564 (1988).
Knight et al., "Transgenic Plant Aequorin Reports the Effects of Touch and Cold–Shock and Elicitors on Cytoplasmic Calcium", Nature 352, 524–526 (1991).
Knight et al., "Recombinant Aequorin as a Probe for Cytosolic Free $Ca^{2+}$ in *Escherichia coli*", FEBS 282, 2, 405–408 (1991).
Lin et al., "Cloning and Functional Expression of a Vascular Smooth Muscle Endothelin 1 Receptor", Proc. Natl. Acad. Sci. U.S.A., 88, 3185–3189 (1991).
Masu et al., "Sequence and Expression of a Metabotropic Glutamate Receptor", Nature, 349, 760–765 (1991).
Morel et al., "Molecular Cloning and Expression of a Rat Vla Arginine Vasopressin Receptor", Nature, 356, 523–526 (1992).
Shimomura et al., "Semi–synthetic Aequorins With Improved Sensitivity to $Ca^{2+}$ Ions", Biochem. J. 261, 913–920 (1989).
Shimomura et al., "Recombinant Aequorin and Recombinant Semi–Synthetic Aequorins", J. Biochem 270, 309–312 (1990).
Shimomura and Johnson, "Regeneration of the Photoprotein Aequorin", Nature 256, 236–238 (1975).
Shimomura and Johnson, "Chemical Nature of Bioluminescence Systems in Coelenterates", Proc. Nat. Acad. Sci. U.S.A. 72, 4, 1546–1549 (1975).
Shimomura and Johnson, "Peroxidized Coelenterazine, the Active Group in the Photoprotein Aequorin", Proc. Nat. Acad. Sci. U.S.A. 75, 6, 2611–2615 (1978).

(List continued on next page.)

Primary Examiner—Jasemine C. Chambers
Assistant Examiner—Deborah J. R. Clark
Attorney, Agent, or Firm—Woodcock Washburn Kurtz Mackiewicz & Norris, LLP

[57] ABSTRACT

Mammalian cells which express apoaequorin and a receptor involved in the modulation of intracellular calcium are provided by the present invention. Transgenic mice in which neuronal cells express aequorin are also provided. Methods of use are provided.

3 Claims, 5 Drawing Sheets

OTHER PUBLICATIONS

Shimomura et al., "Extraction, Purification and Properties of Aequorin, a Bioluminescent Protein from the Luminous Hydromedusan, Aequorea", *J. Cell. Comp. Physiol.* 59, 223–239 (1962).

Siesjö, "Calcium and Cell Death", *Magnesium* 8, 223–237 (1989).

Tsien et al., "Calcium Homeostasis in Intact Lymphocytes: Cytoplasmic Free Calcium Monitored With a New, Intracellularly Trapped Fluorescent Indicator", *J. Cell. Biol.* 94, 325–334 (1982).

Tsien, "A Non–Disruptive Technique for Loading Calcium Buffers and Indicators into Cells", *Nature* 290, 527–528 (1981).

Murphy et al., "Isolation of a cDNA Encoding the Vascular Type–1 Angiotensin II Receptor", *Nature*, 351, 233–236 (1991).

Nakajima–Shimada et al., "Monitoring of Intracellular Calcium in *Saccharomyces cerevisiae* With an Apoaequorin cDNA Expression System", *Proc. Natl. Acad. Sci. U.S.A.* 88, 6878–6882 (1991).

Pritchett et al., "Transient Expression Shows Ligand Subunits", *Science* 242, 1306–1308 (1988).

Pritchett, et al., "Type I and Type II $GABA_A$–Benzodiazepine Receptors Produced in Transfected Cells", *Science* 245, 1389–1392 (1989).

Requena et al., "Intracellular Ionized Calcium Changes in Squid Giant Axons Monitored by Fura–2 and Aequorin", *Ann. N.Y. Acad. Sci.* 639, 112–125 (1991).

Ridgway and Ashley, "Calcium Transients in Single Muscle Fibers", *Biochem. Biophys. Res. Commun.* 29, 229–234 (1967).

Shigemoto et al., "Cloning and Expression of a Rat Neuromedin K Receptor cDNA", *J. Biol. Chem.* 265, 623–628 (1990).

Shimomura and Johnson, "Properties of the Bioluminescent Protein Aequorin", *Biochemistry* 8, 10, 3991–3997 (1969).

Shimomura and Shimomura, "Resistivity to Denaturation of the Apoprotein of Aequorin and Reconstitution of the Luminescent Photoprotein From the Partially Denatured Apoprotein", *Biochem. J.* 199, 825–828 (1981).

Villereal and Palfrey, "Intracellular Calcium and Cell Function", *Annu. Rev. Nutr.* 9, 347–376 (1989).

Prasher et al., "Cloning and Expression of the cDNA for Aequorin, a Bioluminescent Calcium–Binding Protein", *Biochem. Biophys. Res.* 126, 1259–1268 (1985).

Sheu, Y. et al., "Measurement of Intracellular Calcium Using Bioluminescent Aequorin Expressed in Human Cells", *Analytical Biochem.* 1993, 209, 343–347.

Shimomura, O., "Bioluminescence in the Sea: Photoprotein Systems", *Symposium of the Society for Experimental Biology* 1985, 39, 351–372.

R. J. Wall, Transgenic Livestock: Progress and Prospects for the Future, Theriogenology 45:57–68, 1996.

MEASUREMENT OF INTRACELLULAR CALCIUM USING BIOLUMINESCENT APOAEQUORIN EXPRESSED IN MAMMALIAN CELLS

CROSS REFERENCE TO RELATED APPLICATIONS

This application is a continuation-in-part of U.S. patent application Ser. No. 08/034,015 filed Mar. 22, 1993, now abandoned, which is a continuation of Ser. No. 08/015,653 filed Feb. 9, 1993 now abandoned.

BACKGROUND OF THE INVENTION

Intracellular calcium concentration ($[Ca^{++}]i$) acts as a modulator of many important physiological responses and pathophysiological conditions such as excitotoxic brain damage (B. K. Siesjo, *Magnesium* 8, 223 (1989)). In most of these events extracellular signals are received through receptors and converted to changes in $[Ca^{++}]i$. This leads to less well characterized $[Ca^{++}]i$ sensitive changes inside the cell, possibly including modulation of $[Ca^{++}]i$ sensitive kinases, proteases and transcription factors (M. L. Villereal and H. C. Palfrey, *Annu. Rev. Nutr.* 9, 347 (1989)). Measurement of $[Ca^{++}]i$ is essential in understanding such modulation.

Changes in $[Ca^{++}]i$ can be detected using fluorescent dyes (such as fura-2 and indo-1) (R. Y. Tsien, *Nature* 290, 527 (1981); R. Y. Tsien, T. Pozzan, T. J. Rink, *J. Cell. Biol.* 94, 325 (1982), the $Ca^{++}$ sensitive bioluminescent jellyfish protein aequorin (E. B. Ridgway and C. C. Ashley, *Biochem. Biophys. Res. Commun.* 29, 229 (1967), or $Ca^{++}$ sensitive microelectrodes (C. C. Ashley and A. K. Campbell, Eds., *Detection and Measurement of Free $Ca^{2+}$ in cells (Elsevier, North-Holland, Amsterdam,* 1979). Before the advent of the $Ca^{++}$ sensitive dyes, aequorin was the method of choice. However, a major drawback was the necessity of injecting the protein into the cells to be studied, thus limiting its use to the study of single or a limited number of cells. Also there was no commercial source for the purified protein. The lack of a method for determining the exact rather than the relative $[Ca^{++}]i$ was also a hindrance (P. H. Cobbold and T. J. Rink, Biochem. J. 248, 313 (1987). For these reasons $Ca^{++}$ sensitive fluorescent dyes are now more widely used. However, $Ca^{++}$ sensitive dyes also have limitations. Activation of the dye with an excitation beam requires complicated and expensive instruments and limits the use of plastic labware such as microtiter plates. Also since the acetoxymethyl (AM) esters form of the dye crosses the membrane passively, all cells present in the assay system become labelled contributing to the background in some measurements. High autofluorescence is also problematic in some cases (G. Grynkiewicz, M. Poehie, R. Y. Tsien, *J. Biol. Chem.* 260, 6 3440 (1985). Furthermore, fluorescent dyes are subject to compartmentalization and release from cells which can seriously affect interpretation of fluorescent signals from developing or injured cells. Campbell, A. K., et al., *Biochem. J.,* 1988, 252, 143–149. As with aequorin, injection of dye into specific cells limits the number of cells which may be studied (P. H. Cobbold and T. J. Rink, *Biochem. J.* 248, 313 (1987).

Aequorin is the bioluminescent protein complex isolated from the jellyfish *Aequorea victoria*. The protein is abundant in the jellyfish and the purified and crystallized forms of the protein have been extensively studied for many years. The bioluminescent complex is composed of the protein part termed apoaequorin and a chromophore cofactor, coelenterazine (O. Shimomura, F. H. Johnson, Y. Saiga, *J. Cell. Comp. Physiol.* 59, 223 (1962); O. Shimomura and F. H. Johnson, Biochemistry 8, 10, 3991 (1969); O. Shimomura and F. H. Johnson, *Nature* 256, 236 (1975); O. Shimomura and F. H. Johnson, *Proc. Nat. Acad. Sci. U.S.A.* 72, 4, 1546 (1975); O. Shimomura and F. H. Johnson, *Proc. Nat. Acad. Sci. U.S.A.* 75, 6, 2611 (1978); O. Shimomura and A. Shimomura, *Biochem. J.* 199, 825 (1981); O. Shimomura, *Society for Experimental Biology* 351 (1985). Several isoforms of apoaequorin and many analogues of coelenterazine are available (O. Shimomura, B. Musick, Y. Kishi, *Biochem. J.* 261, 913 (1989); O. Shimomura, S. Inouye, B. Musick, Y. Kishi, ibid. 270, 309 (1990). Combinations of these components form complexes with a wide range of $[Ca^{++}]$ sensitivities. From the crystal structure and from other studies the mechanism of photon emission in the presence of elevated $[Ca^{++}]$ is well understood (O. Shimomura, F. H. Johnson, Y. Saiga, *J. Cell. Comp. Physiol.* 59, 223 (1962); O. Shimomura and F. H. Johnson, *Biochemistry* 8, 10, 3991 (1969); O. Shimomura and F. H. Johnson, *Nature* 256, 236 (1975); O. Shimomura and F. H. Johnson, *Proc. Nat. Acad. Sci. U.S.A.* 72, 4, 1546 (1975); O. Shimomura and F. H. Johnson, *Proc. Nat. Acad. Sci. U.S.A.* 75, 6, 2611 (1978); O. Shimomura and A. Shimomura, *Biochem. J.* 199, 825 (1981); O. Shimomura, *Society for Experimental Biology* 351 (1985). Binding of aequorin with trace of amount of free $Ca^{++}$ results in oxidation of coelenterazine, and yields apoaequorin, coelenteramide, $CO_2$, and light. Once the photon has been emitted, the complex must dissociate and the apoaequorin must combine with an activatable cofactor before the complex can emit another photon (O. Shimomura, F. H. Johnson, Y. Saiga, *J. Cell. Comp. Physiol.* 59, 223 (1962); O. Shimomura and F. H. Johnson, *Biochemistry* 8, 10, 3991 (1969); O. Shimomura and F. H. Johnson, *Nature* 256, 236 (1975); O. Shimomura and F. H. Johnson, *Proc. Nat. Acad. Sci. U.S.A.* 72, 4, 1546 (1975); O. Shimomura and F. H. Johnson, *Proc. Nat. Acad. Sci. U.S.A.* 75, 6, 2611 (1978); O. Shimomura and A. Shimomura, *Biochem. J.* 199, 825 (1981); O. Shimomura, *Society for Experimental Biology* 351 (1985).

Cloned DNAs encoding apoprotein have been expressed in bacteria and produced a functional bioluminescent complex when bacterial extracts were combined with the coelenterazine cofactor (M. R. Knight, A. K. Campbell, S. M. Smith, A. J. Trewavas, FEBS 282, 2, 405 (1991); S. Inouye, Y. Sakaki, T. Goto, F. I. Tsuji, *Biochemistry* 25, 8425 (1986). Subsequently other studies have shown that the cDNA can direct the synthesis of the functional apoprotein in plants and yeast as well (M. R. Knight, A. K. Campbell, S. M. Smith, A. J. Trewavas, *Nature* 352, 524 (1991); J. Nakajima-Shimada, H. Lida, F. I. Tsuji, Y. Anraku, *Proc. Natl. Acad. Sci. U.S.A.* 88, 6878 (1991). EPO Application 0 341 477 filed Apr. 24, 1989 taught the expression of aequorin in a mammalian cell system.

In the case of plants it was demonstrated that the coelenterazine cofactor crossed plant cell walls and combined with the apoprotein. A study using mammalian cells loaded with Aequorea mRNA also demonstrated that coelenterazine crossed the cell membrane (A. K. Campbell, A. K. Patel, Z. S. Razavi, F. McCapra, *Biochem. J.* 252, 143 (1988).

While the importance of measuring $Ca^{++}$ concentrations inside the cell is widely acknowledged there has been no ideal way of doing so. Methods of measuring intracellular calcium concentrations, such as for drug screening, which are efficient, accurate and not labor intensive are greatly desired.

SUMMARY OF THE INVENTION

In accordance with the present invention mammalian cells lines are provided which express apoaequorin and a receptor involved in the modulation of intracellular calcium concentration. Apoaequorin is a bioluminescent compound which emits photons in the presence of a cofactor, coelenterazine, and calcium. Apoaequorin and coelenterazine form aequorin. Intracellular calcium concentration can be determined by detection of the photons emitted by the aequorin complex in response to intracellular calcium concentration or changes in intracellular calcium concentration effected by excitation or inhibition of a receptor involved in the modulation of intracellular calcium concentration.

In accordance with one preferred embodiment of the present invention, mammalian cell lines expressing apoaequorin and a receptor involved in the modulation of intracellular calcium are provided.

In accordance with another preferred embodiment of the present invention, transgenic mammals comprising cells expressing apoaequorin are provided.

In accordance with yet another preferred embodiment of the present invention are provided methods of measuring intracellular calcium comprising adding coelenterazine cofactor to mammalian cells expressing apoaequorin and measuring photon emission where emission of photons is indicative of intracellular calcium concentration.

In accordance with still another preferred embodiment of the present invention are provided methods for examining the effect of an agent on a receptor involved in the modulation of intracellular calcium concentration comprising incubating mammalian cells expressing apoaequorin and a receptor involved in the modulation of intracellular calcium concentration with the agent, adding coelenterazine cofactor to the cells, and measuring the photon emission, whereby the emission of photons is indicative of intracellular calcium release.

It is one object of the present invention to provide a useful system for measuring intracellular $Ca^{++}$ concentrations which is at once efficient and accurate.

It is another object of the present invention to provide a system for measuring intracellular $Ca^{++}$ concentrations which does not require injection of the aequorin protein into cells.

It is still another object of the present invention to provide a system for measuring intracellular $Ca^{++}$ concentrations without disruption of the plasma membrane and $Ca^{++}$ homeostasis associated with injection of the aequorin protein into cells.

These and other object of the invention will become apparent in view of the following detailed description of the present invention.

BRIEF DESCRIPTION OF FIGURES

FIG. 5 is a plot of photon emissions following treatment of neuron cells with 100 μl 100 mM $CaCl_2$ and 50 mM EDTA ($CaCl_2$).

DETAILED DESCRIPTION OF THE INVENTION

Figure 1:
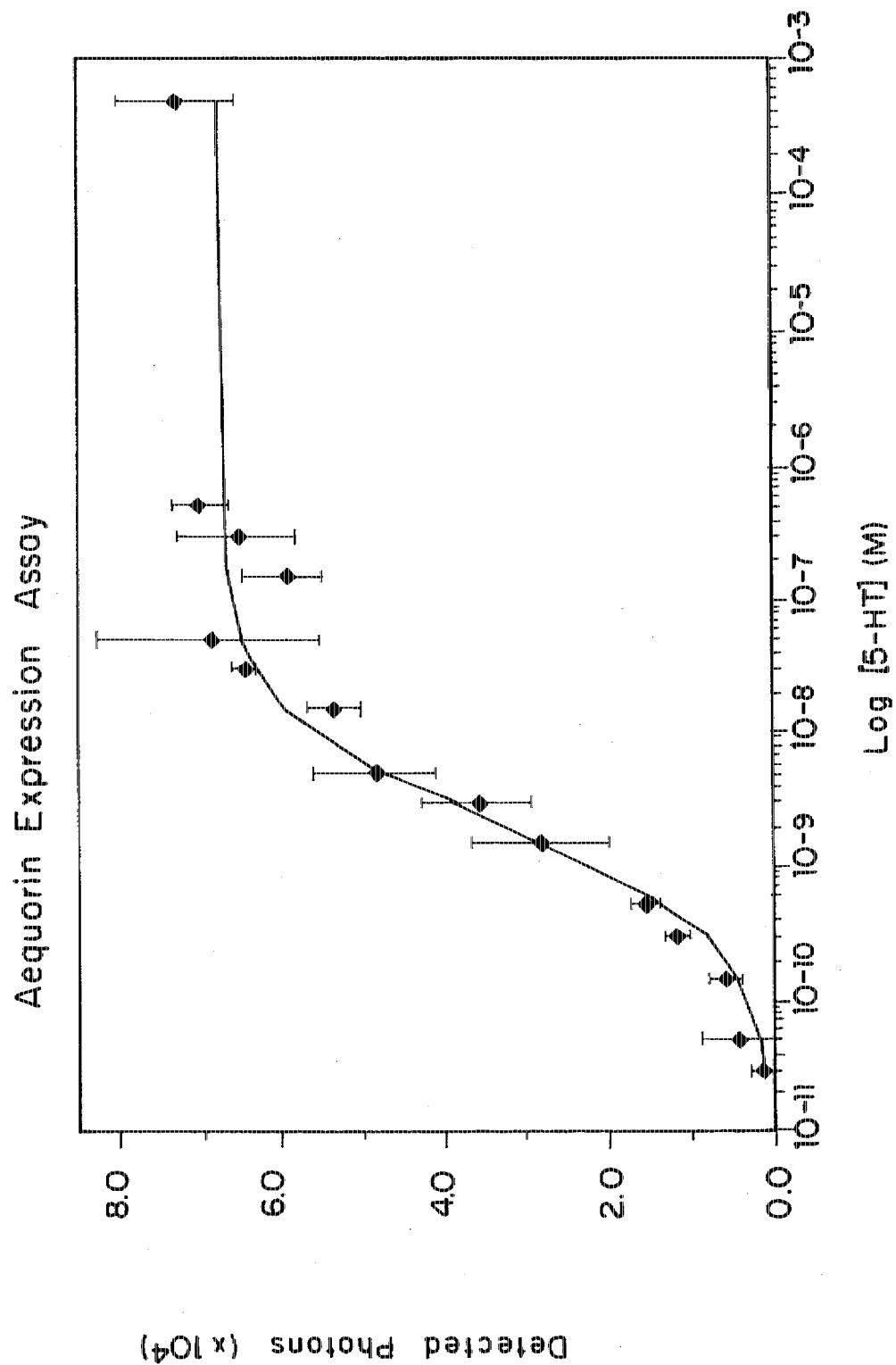
FIG. 1. Serotonin dose dependent light emission of 5-HT$_2$ cDNA and apoaequorin cDNA co-transfected human 293 cells. Cell transfection, harvesting, and aequorin expression assay were performed as described in Example 2 and Example 5. Cells were treated with a wide range of concentrations of serotonin. The line was computer-fitted using a one-site model. Similar experiments were conducted three times. The Kd value from the three experiments is 3.36±0.77 (S.E.M.) nM. The graph shown is representative of these experiments.

The present invention provide mammalian cells which express apoaequorin and a receptor involved in the modulation of intracellular calcium concentration.

Mammalian cells may include any of a broad range of mammalian cells including murine cells and human cells. Preferably, cells of the present invention are human cells. Receptors of the present invention include any and all cell receptors which are involved in the modulation of intracellular calcium. For example, receptors which, when activated, stimulate the intracellular release of calcium, are encompassed by the present invention. Receptors which, when activated, cause a decrease in intracellular calcium concentration are also encompassed herein. In some embodiments of the present invention receptors such as the 5-HT$_2$ receptor, the alpha 1-adrenergic receptor, angiotensin II type-1 receptor, endothelin 1 receptor, luteinizing hormone receptor, metabotropic glutamate receptor, muscarinic receptor m1, muscarinic receptor m3, muscarinic receptor m5, neuromedin K receptor, serontinin 1c receptor and VIa arginine vasopressin receptor are preferred. In preferred embodiments of the present invention the receptor is a 5-HT$_2$receptor.

In a preferred embodiment of the present invention transgenic mammals, such as transgenic mice, comprising cells expressing apoaequorin are provided. Cell-specific gene promoters which regulate the expression of heterologous genes placed downstream can be used to express the apoaequorin protein in a cell specific manner. In some embodiments of the present invention, the apoaequorin gene is inserted downstream from a cell-specific promoter such as the neuron-specific enolase promoter. The term "downstream" is meant to refer to the position of DNA regions relative to the 5' or 3' end of a nucleic acid sequence. Those regions on the 3' side are said to be downstream by those skilled in the art. Expression of the apoaequorin gene, by virtue of its orientation on the gene, and specifically with respect to the cell-specific promoter, is controlled by the cell-specific promoter. Such a system has advantages over dye systems in which the dye is taken up by all the cells in the preparation. Signals from the other cells in the system contribute to the noise of only particular cell types are of interest. Technology for directing proteins to certain subcellular compartments may also be applied to recombinant apoaequorin for the measurement of $Ca^{++}$ in subcellular locations.

Intracellular calcium concentration can be measured in accordance with some embodiments of the present invention by adding coelenterazine cofactor to mammalian cells expressing apoaequorin and measuring photon emission whereby emission of photons is indicative of intracellular calcium concentration. Photon emissions can be recorded by methods known in the art. For example, a commercially available luminometer (Berthold Biolumat LB 9500) may be used to count light emission. Luminescence can also be detected in tissue sections using sensitive photographic equipment which can detect the luminescence at the level of individual processes of the neurons.

Absolute measure of $[Ca^{++}]i$ using aequorin (J. Requena, J. Whittembury, A. Scarpa, J. F. Brinley, Jr., L. J. Mullins, *Ann. N.Y. Acad. Sci.* 639, 112 (1991)) may also be made by the calibration of the aequorin luminescence in vitro and application of that calibration to the signal from the in vivo experiment. The cell lines expressing aequorin are calibrated by testing simultaneously both the dye method and the aequorin method. Similar simultaneous calibration measurements can also be done using calcium sensitive microelectrodes.

In accordance with other methods of the invention, the effect of an agent on a receptor involved in intracellular calcium concentration may be examined.

One important application of this aspect of the present invention is in drug screening where rapid methods of testing for the activity of test compounds are needed. The use of cells of the present invention which express both apoaequorin and a receptor involved in the modulation of intracellular calcium concentration provides methods whereby compounds can be tested for their effect on the release of intracellular calcium. The sensitivity of the system as well as the high signal to noise allows cells in small volumes to be screened. Furthermore, the availability of luminometers that measure cells in microtiter plates provides for testing of thousands of compounds for agonist or antagonist activity. For example, a mammalian cell line co-transfected with a gene coding for apoaequorin and a gene coding for the $5\text{-}HT_2$ receptor which activates intracellular calcium release in cells may be used to study the effect of drugs on the release of intracellular calcium stimulated by the $5\text{-}HT_2$ receptor.

Thus, in accordance with this aspect of the invention, mammalian cells expressing apoaequorin and a receptor involved in the modulation of intracellular calcium are incubated with an agent of interest. Coelenterazine cofactor is added and photon emission is measured whereby the emission of photons is indicative of the amount of intracellular calcium release.

Transgenic mice in which neurons express aequorin may also be used to study neuron function and the effect of agents of interest on neurons in vivo.

Any agent which may be used or disseminated in the mammalian environment are encompassed hereby. Developmental drugs are one particularly pertinent group of agents to which the methods of the present invention are directed. Other agents such as fertilizers, pesticides, herbicides, cleaning agents and the like which may contact mammalian cells and may thereby interact with receptors therein are also subject to methods of the present invention.

The following examples are illustrative but are not meant to be limiting of the present invention.

EXAMPLES

Example 1

Preparation of Apoaequorin Plasmid

Total RNA was prepared from one gram of jellyfish tissue, a courtesy of Dr. Wood, Rutgers University, by the method of acid guanidinium thiocyanate-phenol-chloroform extraction [P. Chomczynski and N. Sacchi, *Analytical Biochemistry* 162, 156 (1987)]. After incubating RNA with murine reverse transcriptase and RNAase inhibitor for 30 minutes at 37° C., the cDNA produced was used as template for PCR [j. Sambrook, E. F. Fritsch, T. Maniatis, Molecular Cloning, a laboratory manual (Cold Spring Harbor Laboratory Press, New York, ed. 2,1989), pp. 7.26–7.29 & pp. 14.18–14.21]. Two oligonucleotides were designed to amplifying the coding region of apoaequorin cDNA, based on the published apoaequorin cDNA sequence by inouye S. et al. (S. Inouye et al., *Proc. Natl. Acad. Sci. U.S.A.* 82, 3154 (1985). The oligonucleotide carrying Xba I restriction site and the other carrying EcoR I restriction site were used as upstream and downstream primer respectively. Thirty cycles of PCR reaction were performed at 95° C. for 30 seconds, 55° C. for 30 seconds, and 72° C. for 1 minute per cycle. The PCR product was digested completely with Xba I and EcoR I, and run on one percent agarose gel. The band with expected size was purified by using activated DEAE-cellulose membrane. This Xba I-EcoR I fragment was cloned into the eukaryotic expression vector pDPneo3 polycloning site producing the plasmid pDPaqneo3.

Example 2

Transfection of Human 293 Cells With Apoaequorin cDNA Construct

Human 293 cells were cultured on 100 mm tissue culture dish in minimum essential medium (MEM) containing 10% charcoal treated fetal bovine serum, 2 mM L-glutamine, 100 units penicillin G sodium per ml, 100 units streptomycin sulfate per ml. DNA mediated transfection was performed when these cells grew to 70% to 80% confluence on the plates. These transfected cells were incubated in 3% $CO_2$, 37° C. incubator overnight. Cells were replenished with fresh medium and transferred to 5% $CO_2$, 37° C. incubator the next day [C. Chen and H. Okayama, *Mol. Cell Biol.* 7, 2745 (1987)] (17).

Example 3

Preparation of $5\text{-}HT_2$ Receptor Plasmid

The $5\text{-}HT_2$ receptor cDNA construct (pDP5ht2neo3) was subcloned into the same expression vector, pDPneo3, used to express the apoaequorin protein.

Example 4

Preparation of α1-Adrenergic Receptor Plasmid

An α1-adrenergic receptor cDNA construct; Cotecchia, et al., *Proc. Natl. Acad. Sci. U.S.A.*, 85, 7159–7163 (1988); is subcloned into the same expression vector pDPneo3, used to express the apoaequorin protein.

Example 5

Preparation of Angiotensin II Type-1 Receptor

An angiotensin II type-1 receptor cDNA construct; Murphy, et al., *Nature*, 351, 233–236 (1991); is subcloned into the same expression vector used to express the apoaequorin protein.

Example 6

Preparation of Endothelin 1 Receptor

An endothelin 1 receptor cDNA construct; Lin, et al., *Proc. Natl. Acad. Sci. U.S.A.*, 88, 3185–3189 (1991); is subcloned into the same expression vector used to express the apoaequorin protein.

Example 7

Preparation of Luteinizing Hormone Receptor

A luteinizing hormone receptor; Gudermann, et al., *J. Biol. Chem.*, 267, 4479–4488 (1992); is subcloned into the same expression vector used to express the apoaequorin protein.

Example 8

Preparation of Metabotropic Glutamate Receptor

A metabotropic glutamate receptor; Masu, et al., *Nature*, 349, 760–765 (1991); is subcloned into the same expression vector used to express the apoaequorin protein.

Example 9

Preparation of Muscarinic Receptors

Muscarinic receptors m1, m3 and m5; T. I. Bonner, *TINS*, 12, 148–151 (1989); are each subcloned into the same expression vector used to express the apoaequorin protein.

Example 10

Preparation of Neuromedin K Receptor

A neuromedin K receptor; Shigemoto, et al., *J. Biol. Chem.*, 265, 623–628 (1990); is subcloned into the same expression vector used to express the apoaequorin protein.

Example 11

Preparation of Serotonin 1c Receptor

A serotonin 1c receptor; Julius, et al., *Science*, 241, 558–564 (1988); is subcloned into the same expression vector used to express the apoaequorin protein.

Example 12

Preparation of VIa Arginine Vasopressin Receptor

A VIa arginine vasopressin receptor; Morel, et al., *Nature*, 356, 523–526 (1992) is subcloned into the same expression vector used to express the apoaequorin protein.

Example 13

Cotransfection of Human 293 Cells with Apoaequorin cDNA Construct and 5-HT$_2$ Construct

DNA from the apoaequorin plasmid (pDPaqneo3) and the 5-HT$_2$ plasmid (pDP5ht2neo3) were mixed in equal portions in the transfection solution immediately before transfection. Transfection was performed as described in Example 2. Using the co-transfection procedure it has been demonstrated that the vast majority of cells that take up any DNA take up both DNAs (D. B. Pritchett et al., *Science*, 242, 1306 (1988), D. B. Pritchett, et al., ibid, 245, 1389 (1989).

Example 14

Cotransfection of Human 293 Cells with Apoaequorin cDNA Construct and Receptor Construct

DNA from the apoaequorin plasmid (pDPaqneo3) and a receptor plasmid prepared in accordance with one of Examples 4–12 are mixed in equal portions in the transfection solution immediately before transfection. Transfection is performed as described in Example 2.

Example 15

Apoaequorin Expression Assay

Two days after the transfection, cells were washed twice with phosphate buffered saline (PBS). Cells were then harvested by ice-cold PBS and rubber policeman. After centrifugation at 1,600 r.p.m. for 5 minutes, the pellet was dissolved in Ca$^{++}$-free AqH buffer (120 mM NaCl, 4.8 mM KCl, 1.2 mM KH$_2$PO$_4$, 25 mM Hepes, 0.1% bovine serum albumin, pH 7.4) at a concentration about 10 million cells per 1 ml solution. Tubes containing cells were wrapped with aluminum foil. Coelenterazine was a generous gift from Dr. Kishi, Harvard University and Dr. Shimomura, Marine Biological Laboratory. It was stored at −70° C., dissolved in methanol immediately before use, and kept in the dark at all times. The concentration of coelenterazine was estimated by the measurement of absorbance at 434 nanometer [the molar absorptivity$_{434}$=8,900 M$^{-1 \cdot cm-1}$; K. Hori, H. Charbonneau, R. C. Hart, M. J. Cormier. *Proc. Natl. Acad. Sci. U.S.A.* 74, 4285 (1977)]. Aequorin was reconstituted incubating these apoaequorin cDNA transfected cells with 10 μM coelenterazine in the dark room temperature for 30 minutes. Unincorporated coelenterazine was washed away after incubation by adding 25 ml Ca$^{++}$-free AqH buffer to each sample and centrifugating at 1,600 r.p.m. Samples were centrifuged again and pellets of 293 cells were dissolved in Ca$^{++}$-free AqH buffer. The final concentration of cells was approximately 10 million per 1 ml solution. For light emission measurement, 100 μl of cell sample was mixed with equal volume of appropriate reagent in a 2 ml glass tube immediately before inserted into the luminometer (Berthold Biolumat LB 9500). Counting of light emission started immediately after the glass tube insertion. The number of photons emitted during the first 30 seconds was integrated by the luminometer and shown on the screen. The time course of light emission was recorded on a chart recorder and a Mackintosh computer using the MacLab Chart/4 V3.1.3 program for further analysis.

The addition of Ca$^{++}$ to the cells transfected with pDPaqneo3 and incubated with cofactor caused a rapid and dramatic increase in the photons detected by the luminometer. Cells transfected with plasmids not containing apoaequorin cDNA sequences and untransfected cells (data not shown) showed no rise in the emission of photons upon the addition of Ca$^{++}$. Cells transfected with the pDPaqneo3 construct not incubated with coelenterazine cofactor showed no increase of light emission. The addition of EDTA to the buffer to chelate the available Ca$^{++}$ also prevented the increase in photon emission from pDPaqneo3-transfected cells (data now shown). Table 1 sets forth this data.

TABLE 1

| Aequorin Expression Assay (Detected Photons) | | | |
|---|---|---|---|
| | pDPaqneo3 & pDP5ht2neo3 | pDP5ht2neo3 | pDPaqneo3 | pDP3 |
| 500 nM 5-HT$_2$ | 79,840 ± 3,342 | 1,308 ± 339 | 6,150 ± 2,360 | 1,599 ± 45 |
| 50 nM Ca$^{++}$ | ND | 1,346 ± 167 | 293,209 ± 72,032 | 1,607 ± 254 |
| Buffer | 11,558 ± 4,265 | 1,488 ± 175 | 5,971 ± 1,662 | 1,799 ± 149 |

Example 16

Measurement of Calcium Released from Intracellular Stores Following Stimulation by Serotonin

The cotransfected cells of Example 4 were tested for the production of photons as described in Example 15 after treatment of the cells with serotonin. We used the transfected serotonin 5-HT$_2$ receptor to stimulate phosphoinositide hydrolysis and intracellular Ca$^{++}$ release. This receptor stimulates such release in normal tissue and in transfected 293 cells. Both the stimulation of phosphoinositide hydrolysis and the release of Ca$^{++}$ (using fura-2) have been measured directly in transfected cells.

Cells co-transfected with pDPaqneo3 and pDP5ht2neo3 showed a dramatic rise in photon emission upon the addition of serotonin to the cells. Photon emissions as large as 40 photons per cell were detected by saturating concentration (500 µM) of serotonin. These responses were smaller than the maximum responses recorded from pDPaqneo3-transfected cells stimulated by Ca$^{++}$ directly. The responses varied 3-4 fold between transfections but showed little variation in the same experiment. Cells transfected with pDPaqneo3 only or pDP5ht2neo3 only, or pDP3 vector only showed no increase of photo emission upon serotonin treatment. Data is set forth in Table 1 (above).

Example 17

Test for Dose Dependent Response and Specificity to Serotonin

Cells cotransfected with pDPaqneo3 and pDP4ht2neo3 were treated with from 0.05 nM to 500 µM of concentrations of serotonin. Intracellular calcium concentration was measured as described in Example 15.

The response to serotonin was saturable and dose dependent showing a half maximal response at 3.36±0.77 (S.E.M.) nM of serotonin. Data is set forth in FIG. 1. This concentration agrees with the concentration of serotonin that produces half maximal response as measured by hydrolysis of phosphoinositides.

Figure 2:
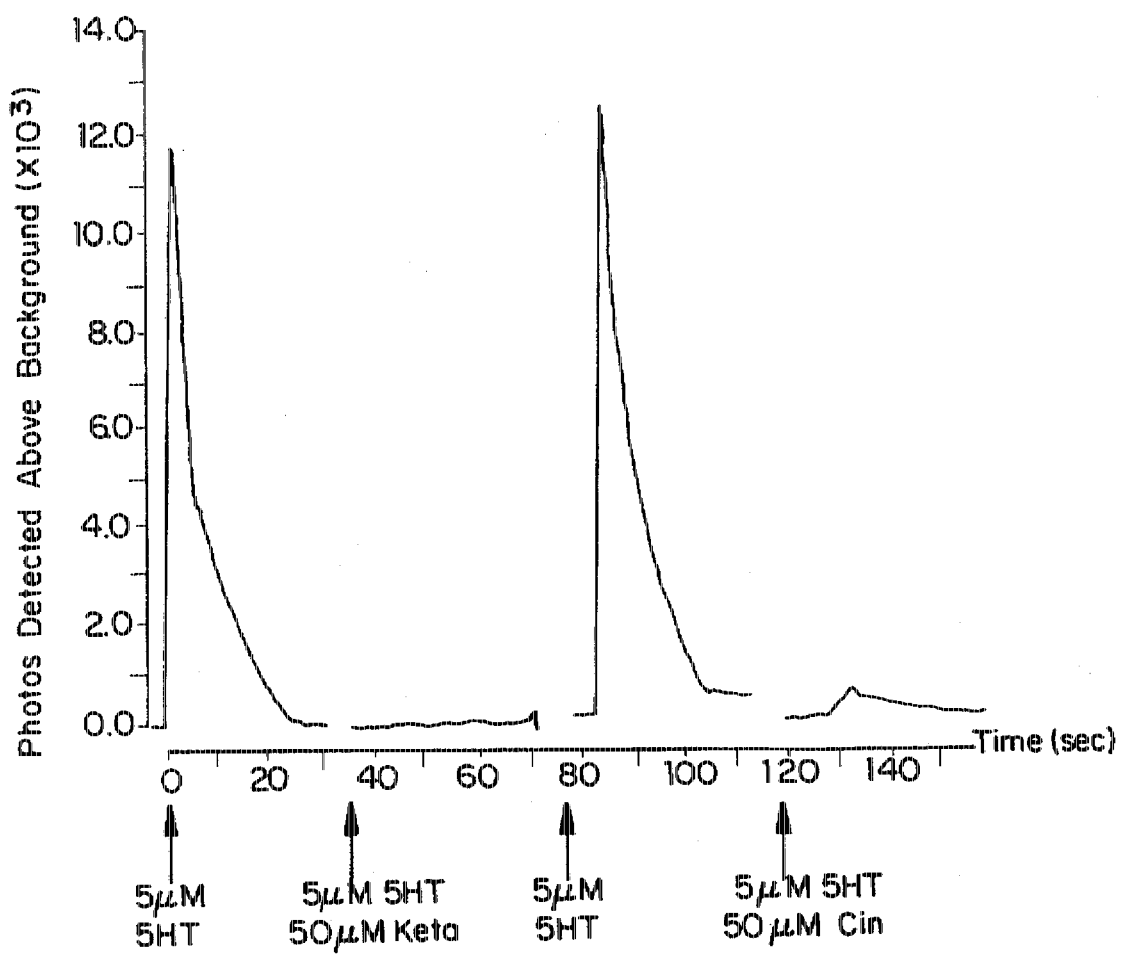
FIG. 2. Antagonist inhibition of light emission from 10 μM serotonin treated apoaequorin cDNA and 5-HT$_2$ cDNA co-transfected human 293 cells. Human 293 cells co-transfected with apoaequorin cDNA and 5-HT$_2$ cDNA emitted light upon 10 μM 5-HT treatment. The response was inhibited by 50 μM cinanoerin or 50 μM ketanserin. Cells were incubated with antagonists for 30 seconds before adding serotonin. Other procedures for cell transfection, harvesting and aequorin expression assay were carried out as described in Example 2 and Example 15.

To ensure that this response to serotonin was being mediated through the 5-HT$_2$ receptors we tested the response to serotonin in the presence of antagonists that are specific for the 5-HT$_2$ receptor. The antagonists cinanserin and ketanserin both inhibited the emission of photons in response to serotonin at 50 µM, concentrations that are consistent with a block of 5-HT$_2$ receptors. Data is set forth in FIG. 2.

Example 18

Measurement of Calcium Released from Intracellular Stores Following Stimulation by Norepinephrine The cotransfected cells of Example 14 expressing α1-adrenergic receptor are tested for the production of photons as described in Example 15 after treatment of the cells with norepinephrine.

Example 19

Measurement of Calcium Released from Intracellular Stores Following Stimulation by Angiotensin II The cotransfected cells of Example 14 expressing angiotensin II type-1 receptor are tested for the production of photons as described in Example 15 after treatment of the cells with angiotensin II.

Example 20

Measurement of Calcium Released from Intracellular Stores Following Stimulation by Endothelin 1

The cotransfected cells of Example 14 expressing the endothelin 1 receptor are tested for the production of photons as described in Example 15 after treatment of the cells with endothelin 1.

Example 21

Measurement of Calcium Released from Intracellular Stores Following Stimulation by Luteinizing Hormone The cotransfected cells of Example 14 expressing the luteinizing receptor are tested for the production of photons as described in Example 15 after treatment of the cells with luteinizing hormone.

Example 22

Measurement of Calcium Released from Intracellular Stores Following Stimulation by Metabotrophic Glutamate The cotransfected cells of Example 14 expressing the metabotrophic glutamate receptor are tested for the production of photons as described in Example 15 after treatment of the cells with metabotrophic glutamate.

Example 23

Measurement of Calcium Released from Intracellular Stores Following Stimulation by Neuromedin K The cotransfected cells of Example 14 expressing the neuromedin K receptor are tested for the production of photons as described in Example 15 after treatment of the cells with neuromedin K.

Example 24

Measurement of Calcium Released from Intracellular Stores Following Stimulation by Serotonin 1c The cotransfected cells of Example 14 expressing the serotonin 1c receptor are tested for the production of photons as described in Example 15 after treatment of the cells with serotonin 1c.

Example 25

Measurement of Calcium Released from Intracellular Stores Following Stimulation by VIa Arginine Vasopressin The cotransfected cells of Example 14 expressing the VIa arginine vasopressin receptor are tested for the production of photons as described in Example 15 after treatment of the cells with VIa arginine vasopressin.

Example 26

Production of Cell Line Expressing Apoaequorin

Human 293 cells were transfected with pDPaqneo3 by the same method described in Example 2. Two days after the transfection cells were trypsinized and diluted to 10 or to 100 time. The next day the medium was replaced with minimum essential medium containing 500 µg of genticin per ml. Medium containing the same concentration of genticin was replaced every two to three days. Once the cells grow up to well isolated colonies, those colonies were transferred to new plates by trypsin-presoaked sterile Whatman paper. When the cells had grown to a number (10$^7$ cells) sufficient for analysis, they were harvested and assayed for aequorin expression as described in Example 15. After about 1 month, nineteen G418 resistant clones were selected and tested. Seventeen of nineteen clones tested expressed apoaequorin. Some clones appear to have some morphological change which are probably due to the random selection of a variant, since these morphological changes have been observed for other clonal cell lines stably transfected with the plasmid vector only. Otherwise all cells survived well. Clone J was cultured continually in MEM without geneticin for three months and still expresses similar levels of apoaequorin.

Example 27

Production of Cell Line Expressing Apoaequorin and 5-HT$_2$

Human 293 cells are transfected with pDPaqneo3 and pDP5ht2neo3 by the same method described in Example 4. Two days after the transfection cells are trypsinized and diluted to 10 or to 100 time. The next day the medium is replaced with minimum essential medium containing 500 μg of genticin per ml. Medium containing the same concentration of genticin is replaced every two to three days. Once the cells grow up to well isolated colonies, those colonies are transferred to new plates by trypsin-presoaked sterile Whatman paper. When the cells have grown to a number ($10^7$ cells) sufficient for analysis, they are harvested and assayed for aequorin expression as described in Example 15.

Example 28

Production of Cell Line Expressing Apoaequorin and a Receptor

DNA from the apoaequorin plasmid (pDPaqneo3) and a receptor plasmid prepared in accordance with one of Examples 4–12 are mixed in equal portions in the transfection solution immediately before transfection. Transfection is performed as described in Example 4. Two days after the transfection cells are trypsinized and diluted to 10 or to 100 time. The next day the medium is replaced with minimum essential medium containing 500 μg of genticin per ml. Medium containing the same concentration of genticin is replaced every two to three days. Once the cells grow up to well isolated colonies, those colonies are transferred to new plates by trypsin-presoaked sterile Whatman paper. When the cells have grown to a number ($10^7$ cells) sufficient for analysis, they are harvested and assayed for aequorin expression as described in Example 15.

Example 29

Apoaequorin PNSEaq Plasmid Construct

Figure 3:
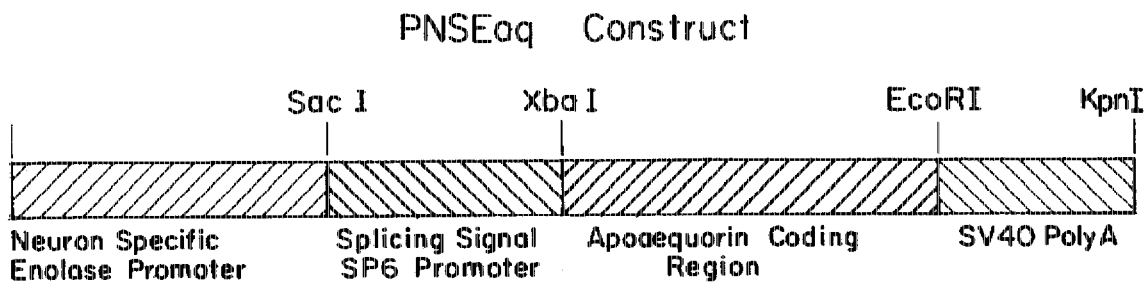
FIG. 3 is a schematic drawing of the PNSEaq vector.

An apoaequorin plasmid was prepared essentially as described in Example 1 to produce the construct as shown in FIG. 3. The CMV promoter incorporated into the pDPaqneo3 plasmid was replaced with a promoter specific for neurons, neuron specific enolase promoter (NSE). The resulting plasmid, PNSEaq, is expressed only in neurons.

Example 30

Preparation of Transgenic Mice Expressing Apoaequorin

To produce transgenic mice with apoaequorin gone construct one-cell zygotes were obtained.

Female mice (2 to 12 months of age) were induced to superovulate by intraperitoneal injection of pregnant mare serum (5IU) followed 48 hours later by injection of human chorionic gonadotrophin (5IU). Superovulated females were subsequently mated with males (2 to 12 months of age) under conditions in which a constant light-dark cycle is maintained. Females were checked for the presence of a vaginal plug the morning after mating. Pregnant females (approximately 0.5 days post coitus) were killed by cervical dislocation. The oviducts were removed, dissected open and incubated in M2 medium containing hyaluronidase (300 μg/ml) for several minutes at room temperature to release fertilized eggs. The embryos were then transferred to M16 medium and maintained at 37° C. until needed for microinjection. DNA for injection was prepared as described in Example 29. DNA was purified by centrifugation in CsCl and dialysis. The fertilized eggs were injected with the DNA using a micromanipulator with a holding pipette and a microinjection pipette both attached to the stage of an inverted microscope equipped with Nomarski differential interference contrast optics. The male pronucleus was injected with about 2 picoliters of the DNA solution containing 2 μg/ml and about 600 copies per embryo of apoaequorin gone in Tris/EDTA buffer. The eggs were transferred on the same day or cultured to the two cell stage and transferred the next day into the oviduct of a 0.5 day post-coitus pseudopregnant female.

Figure 4:
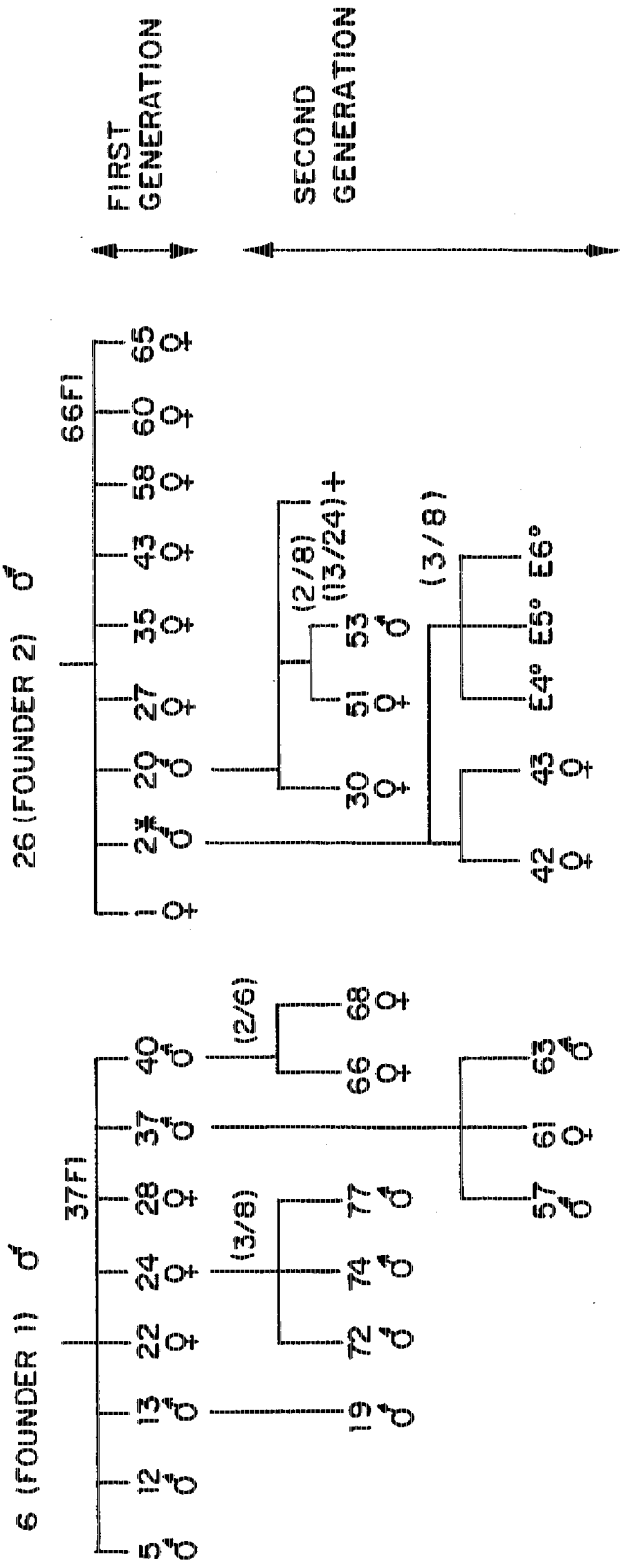
FIG. 4 is schematic drawing of the pedigree of two generations of transgenic mice.

Progeny are tested for expression of apoaequorin. Brain tissue is extracted and tested using PCR analysis using the PCR primers. The pedigree of two generations of mice is set forth in FIG. 4. These mice were tested for expression of apoaequorin gene by PCR using PCR primer pairs upstream and downstream from the aequorin gene.

Lines of transgenic mice that express apoaequorin gene were cross-bred with non-transgenic B6XSJLF$_1$ female mice to generate lines expressing higher levels of the gene.

Example 31

Preparation of primary neuron cultures

Transgenic mice were prepared as described in Example 30. A transgenic mouse was mated with non-transgenic mouse B6XSJLF$_1$ female mouse. The whole brains were removed from 19 day old mouse embryos and used to make primary neuronal cultures and incubated in minimum essential medium containing 500 μg genticin per ml. After ten days, cells were removed from plates, mixed with colenterazine and tested for aequorin expression using an expression assay.

Example 32

Effect of CaCl$_2$ on Primary Neuron Culture

Embryos resulting from mating transgenic mouse no.2 and a non-transgenic B6XSJLF$_1$ female mouse were used to prepare a primary neuron culture as described in Example 31.

Figure 5A:
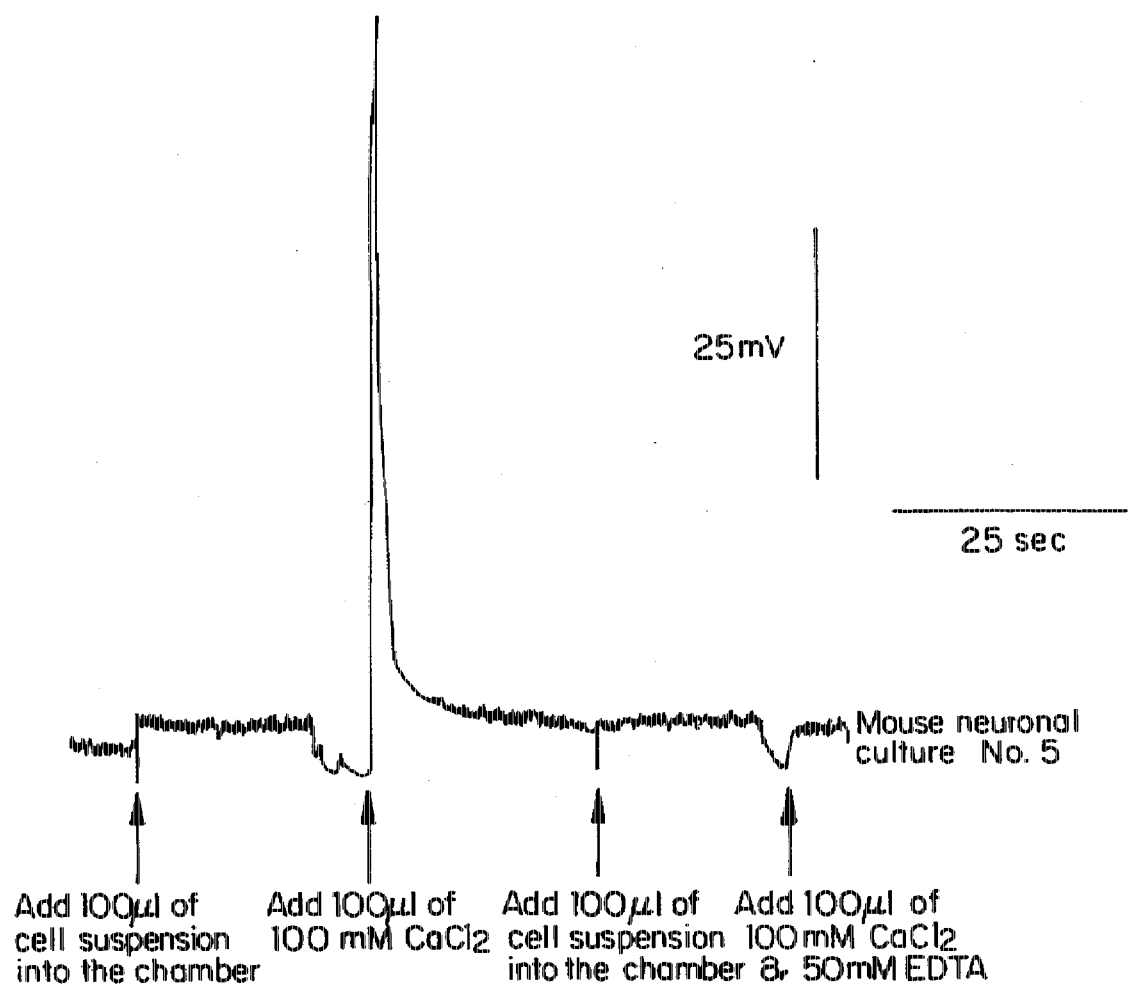
FIG. 5A shows the effect of $CaCl_2$ on mouse neuronal culture number 5 (derived from embryos taken from cross of transgenic mouse no. 2 X non-transgenic B6XSJLF$_1$).
Figure 5B:
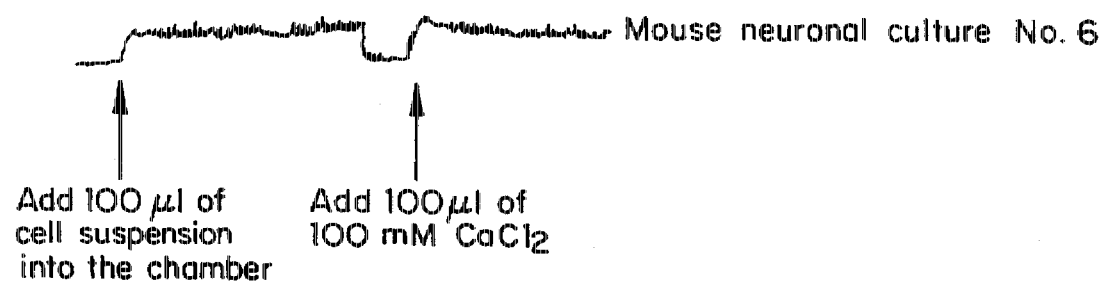
FIG. 5B shows the effect of $CaCl_2$ on mouse neuronal culture number 6 (control).

100 μl of 100 mM CaCl$_2$ was added to the cell culture and photon emission was measured as described in Example 15. As shown in FIG. 5A, addition of CaCl$_2$ resulted in an increase in cell excitotoxicity. Control neuron cell culture (non-transgenic neuronal culture no. 6) showed no excitotoxic effect following the addition of CaCl$_2$.

Example 33

Effect of CaCl$_2$ and BR-A23187 on Primary Neuron Culture

Embryos resulting from mating transgenic mouse no. 20 and a non-transgenic B6XSJLF$_1$ female mouse were used to prepare a primary neuron culture as described in Example 31.

Figure 6A:
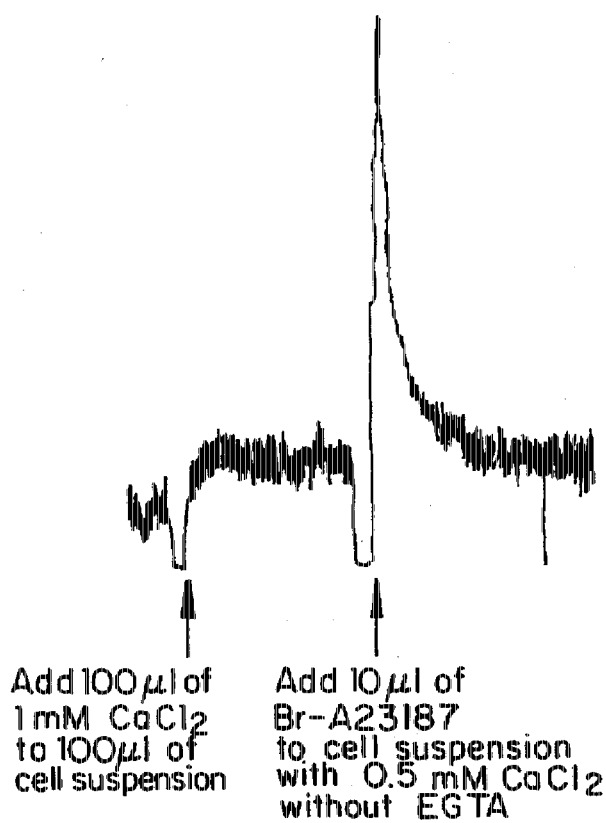
FIG. 6A is a plot of photon emissions following treatment of neuron cells with $CaCl_2$ and Br-A23187.
Figure 6B:
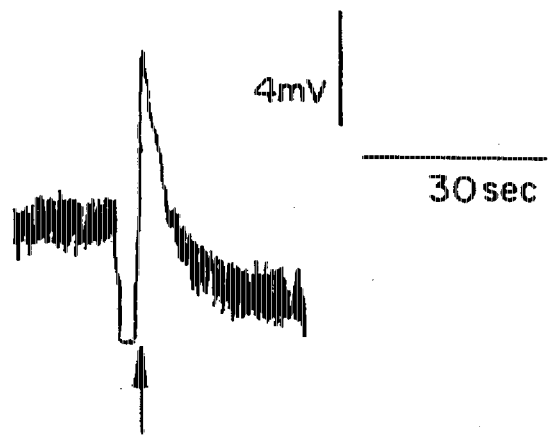
FIG. 6B is a plot of photon emissions following treatment of neuron cells with $CaCl_2$, EGTA and Br-A23187 Neuron cells were derived from embryos taken from cross of transgenic mouse no. 20 X non-transgenic B6XSJLF$_1$).

100 μl of 100 mM CaCl$_2$ was added to the cell culture and photon emission was measured as described in Example 15. Thereafter 10 μl (1 mg/ml PBS) Br-A23187 and 0.5 mM CaCl$_2$ were added to the cell culture. The drug Br-A23187 opens calcium channels. As shown in FIG. 6A addition of Br-A23187 and CaCl$_2$ resulted in increased excitotoxicity. As shown in FIG. 6B, addition of Br-A23187 with 0.5 mM CaCl$_2$ and 50 mM EGTA also resulted in increased excitotoxicity

What is claimed is:

1. A transgenic mouse whose cells comprise a gene encoding apoaequorin, wherein neuron cells of said mouse express said apoaequorin and wherein intracellular calcium concentration in said neuron cells which, upon isolation and culturing, can be determined by detection of photons emitted by an aequorin complex comprising said apoaequorin.

2. The transgenic mouse of claim 1 wherein the apoaequorin gene is downstream from a neuron-specific promoter, and is operably linked thereto.

3. The transgenic mouse of claim 2 wherein the neuron-specific promoter is an enolase promoter.

* * * * *

UNITED STATES PATENT AND TRADEMARK OFFICE
CERTIFICATE OF CORRECTION

PATENT NO. : 5,714,666
DATED : February 3, 1998
INVENTOR(S) : Dolan B. Pritchett, Sharon B. Pritchett and Yeong-An Sheu It is certified that error appears in the above-identified patent and that said Letters Patent is hereby corrected as shown below:

Col. 6, line 18, "inouye" should be capital --Inouye--.

Col. 7, line 54, "(pDPSht2neo3)" should be --pDP5ht2neo3--.

Col. 11, line 55, "gone" should be --gene--.

Signed and Sealed this

Twenty-eighth Day of April, 1998

Attest:

BRUCE LEHMAN

Attesting Officer

Commissioner of Patents and Trademarks